Figure 1:
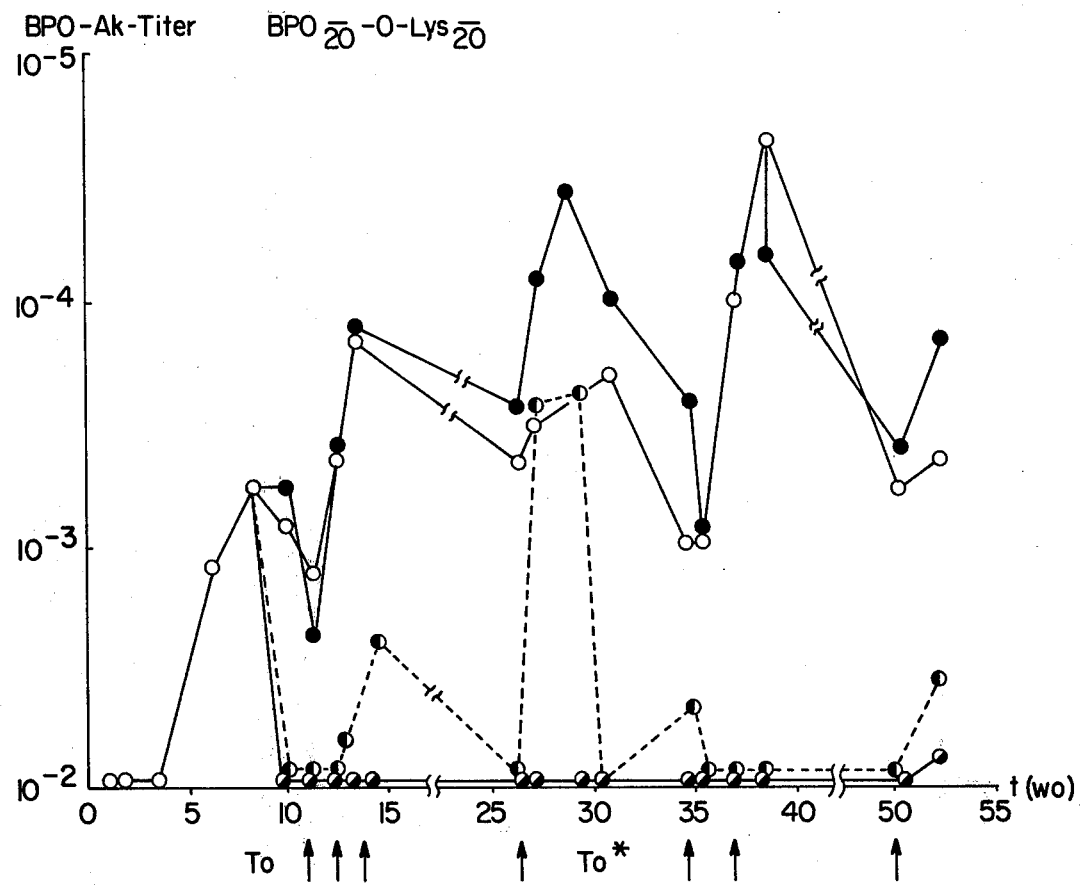

United States Patent [19]

de Weck et al.

[11] 4,168,263
[45] Sep. 18, 1979

[54] POLYPEPTIDE DERIVATIVES

[75] Inventors: Alain de Weck, Marly-le-Petit; Conrad H. Schneider, Thun, both of Switzerland

[73] Assignee: Hoffmann-La Roche Inc., Nutley, N.J.

[21] Appl. No.: 836,169

[22] Filed: Sep. 23, 1977

[30] Foreign Application Priority Data

Sep. 28, 1976 [CH] Switzerland .................. 12238/76

[51] Int. Cl.² ............ C07C 103/52; A61K 37/02
[52] U.S. Cl. ........................... 260/112.5 R; 424/177
[58] Field of Search ........................... 260/112.5 R

[56] References Cited

U.S. PATENT DOCUMENTS

| 2,625,543 | 1/1953 | Ruskin | 260/112.5 R |
| 3,592,804 | 7/1971 | Quitt et al. | 260/112.5 R |
| 3,867,365 | 2/1975 | Stahmann et al. | 260/112.5 R |

OTHER PUBLICATIONS

Schneider, et al., Helv. Chim. Acta, 49, 1966, pp. 1695–1705.
N. Chiorazzi, et al., Proc. Natl. Acad. Sci. USA, 73, 1976, pp. 2091–2095.
Schneider, et al., Nature, 1965, pp. 57–59.

Primary Examiner—Delbert R. Phillips
Attorney, Agent, or Firm—Jon S. Saxe; Bernard S. Leon; Frank P. Hoffman

[57] ABSTRACT

There is presented peptide derivatives comprising polypeptides to which are bound via its functional sidechains penicilloyl residues of the formula

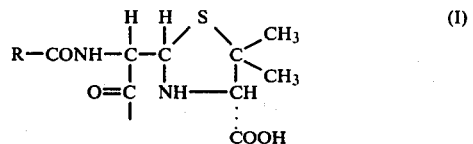

wherein R signifies 2-pentenyl, n-pentyl, n-heptyl, allylthiomethyl, 5-amino-5-carboxypentyl, benzyl, α-carboxy benzyl, α-aminobenzyl, phenoxy benzyl, phenoxymethyl, α-phenoxy ethyl, α-phenoxypropyl, 2,6-dimethoxyphenyl, 2-ethoxy-1-naphthyl, 3-carboxy-2-quinoxazinyl, 5-methyl-3-phenyl-4-isoxazolyl, α-amino-p-hydroxy benzyl, 3-(2-chlorophenyl)-5-methyl-4-isoxazolyl, 3-(2,6-dichlorophenyl)-5-methyl-4-isoxazolyl, 3-(2-chloro-6-fluoro-phenyl)-5-methyl-4-isoxazolyl, α-carboxy-3-thienylmethyl or α-sulphonylbenzyl.

The peptide derivatives exhibit antiallergic activity.

9 Claims, 1 Drawing Figure

POLYPEPTIDE DERIVATIVES

DESCRIPTION OF THE INVENTION

The present invention is concerned with polypeptide derivatives and a process for the manufacture thereof.

In the treatment of allergies it is an objective to overcome their real causes, this objective hitherto having not been achieved or having been achieved only to some extent. Instead of this, only their symptoms have in general been overcome. The cause of all true allergies lies in the formation, induced in an organism by antigens, of antigen-specific antibodies which then react in a specific manner in a renewed contact with these same antigens. There thus occurs an immune mechanism which, however, proceeds in an undesirable manner since undesirable effects appear for the organism. When, in the case of the antigens, there come into consideration, for example, pharmaca, then these effects are known as "medicament allergies" which manifest themselves in skin eruptions, oedemas, anaphylactic reactions, fever and eosinophilia. Especially known and feared are those reactions in connection with the repeated administration of penicillins, by reason of which the possibility of the use of these so therapeutically active compounds which is safe for the patients is considerably limited under certain conditions.

Organisms (under which term there are to be understood human beings as well as animals) which already possess antigen-specific antibodies which can react with these same antigens, whereby the undesirable allergic reaction is produced, are said to be "sensitized". Organisms which possess no antigen-specific antibodies or whose already present antibodies can no longer react with the specific antigens in the sense of an allergic reaction are said to be "unsensitized" or "desensitized".

The causative treatment of allergies accordingly lies in the elimination of sensitization manifested by antibody formation or the prevention of such a sensitization.

The measures, which hitherto had to be used in animal experiments in order to generate a long-lasting specific immunological tolerance in the case of non-sensitized individuals, are so drastic or complicated that they have found no place in human medicine. Even more difficult is the situation regarding the generation of a long-lasting specific immunological tolerance in the case of already sensitized individuals.

The possibility of achieving an immunological tolerance in the case of non-sensitized mice by administration of linear copolymers of D-amino acids has been known for several years [Janeway & Humphrey, Isr. J. Med. Sci. 5, 185–195 (1969)]. On the other hand, a completely new method of achieving an immunological tolerance and a specific elimination of the antibody formation in the case of already sensitized mice resulted from experiments of Katz et al. [J. Exp. Med. 136, 1404–1429 (1972)], which showed that the administration of a 2,4-dinitrophenyl derivative of a copolymer of D-glutamic acid and D-lysine, with an average molecular weight of the polypeptide of 115,000, to mice induced a specific 2,4-dinitrophenyl tolerance independently of their immunological condition at this point in time.

In the recent work of Chiorazzi et al. [Proc. Nat. Acad. Sci. 73, 2091–2095 (1976)] it has been shown that in the case of mice, which are not only unsensitized but also sensitized to the benzylpenicilloyl group, there can be achieved a highly specific and long-lasting tolerance towards benzylpenicillin by administration of a benzylpenicilloyl derivative of a polypeptide of D-glutamic acid and D-lysine (average molecular weight 50,000, ratio D-glutamic acid: D-lysine=60:40). Based on these findings there may now result an entirely new possibility of effectively eliminating penicillin allergies also in the case of human beings.

It has now been found in accordance with the present invention that the findings of Chiorazzi et al. can be generalized and, moreover, that even the administration of other penicilloyl conjugates can bring about a long-lasting tolerance towards penicillins in the case of human beings and animals. The novel penicilloyl conjugates differ from the prior-known conjugates either in that they carry other penicilloyl residues and/or in that the average molecular weight of the peptide component is higher or lower and/or in that their amino acid composition is different.

The present invention is accordingly concerned with novel polypeptide derivatives (referred to herein as tolerogens) of a polypeptide, preferably having a linear structure, to which are bound via its functional side-chains penicilloyl residues (referred to herein as haptens) and which optionally carries other acyl residues on nonpenicilloylated side-chains, with the exception of a benzylpenicilloyl derivative of a polypeptide of D-glutamic acid and D-lysine with an average molecular weight of 50,000 and a ratio of D-glutamic acid to D-lysine of 60:40.

The molecular weight of the peptide component can be that of a tetrapeptide up to $5.10^5$.

As the polypeptides there preferably come into consideration on the one hand those having an average molecular weight up to about 45,000, especially of 1,000 to 10,000 and particularly of 2,000 to 5,000, and on the other hand those having an average molecular weight of about 55,000 to about $5.10^5$, especially of 90,000 to 250,000 and particularly of 93,000 to 210,000.

The polypeptide chains can be built up from the known amino acids (D- and/or L-form) in optional sequence, the preferred amino acids being those having the D-form. Especially preferred is the use of a high proportion of amino acids having a functional side-chain such as, for example, D- and L-lysine, D- and L-tyrosine, D- and L-glutamic acid or -glutamine, D- and L-aspartic acid or -asparagine, D- and L-serine, D- and L-threonine, and the like. Lysine and ornithine may be mentioned as examples of especially suitable amino acids having side-chains capable of substitution. Examples of amino acids which can likewise be used in the synthesis of the polypeptide chains but which possess no side-chains capable of substitution are glycine, D- and L-alanine, D- and L-valine, D- and L-leucine and D- and L-isoleucine.

As the hapten components there come into consideration penicilloyl residues in the widest sense; that is to say, all penicilloyl residues of penicillins which can be the cause of undesirable allergic reactions. For example, this penicilloyl residue can have the following general formula

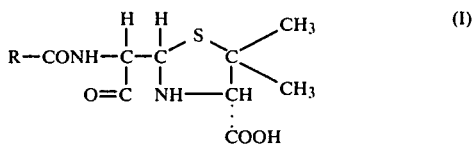

wherein R signifies 2-pentenyl, n-pentyl, n-heptyl, allylthiomethyl, 5-amino-5-carboxypentyl, benzyl, α-carboxybenzyl, α-aminobenzyl, phenoxybenzyl, phenoxymethyl, α-phenoxyethyl, α-phenoxypropyl, 2,6-dimethoxyphenyl, 2-ethoxy-1-naphthyl, 3-carboxy-2-quinoxazinyl, 5-methyl-3-phenyl-4-isoxazolyl, α-amino-p-hydroxybenzyl, 3-(2-chlorophenyl)-5-methyl-4-isoxazolyl, 3-(2,6-dichlorophenyl)-5-methyl-4-isoxazolyl, 3-(2-chloro-6-fluorophenyl)-5-methyl-4-isoxazolyl, α-carboxy-3-thienylmethyl or α-sulphonylbenzyl.

The ratio of penicilloyl residues to side-chains capable of substitution (e.g., in the case of lysine) in the tolerogens can be regulated by the use of appropriate amounts of starting materials in the synthesis. With a view to obtaining tolerogens having a specific action which is as high as possible, as high as possible a loading, preferably a 100% loading, of the carrier polypeptide with hapten groups is desirable. The polypeptide carrier can carry on the reactive side-chains ε-NH$_2$ groups such as are derived, for example, from lysine, as well as also residues which are suitable, for example, for increasing the solubility or preventing undesirable effects which may appear when a large number of free amino groups are present in the molecule. Examples of suitable groups are, in particular, acyl residues derived from monocarboxylic acids and dicarboxylic acids such as acetic acid, propionic acid, malonic acid and succinic acid, with succinic acid being preferred.

Examples of tolerogens provided by the present invention are the following polypeptide derivatives (BPO representing benzylpenicilloyl and the average molecular weight of the peptide component being given in brackets):

| | |
|---|---|
| BPO$_{20}$-D-Lys$_{20}$ | MW. 9 240 (3000) |
| BPO$_{20}$-L-Lys$_{20}$ | MW. 9 240 (3000) |
| BPO$_5$-Suc$_{15}$-D-Lys$_{20}$ | MW. 5 730 (3000) |
| BPO$_5$-L-Lys$_4$-Gly | MW. 2 259 |
| BPO$_{40}$-Suc$_{60}$-poly-D-Lys | MW. 380000 (150000) |
| BPO$_{38}$-poly-D-Glu$_{48}$-D-Lys$_{38}$-D-Tyr$_{14}$ | MW. 310000 (160000) |
| BPO$_{39}$-poly-D-Glu$_{55}$-D-Lys$_{39}$-D-Tyr$_6$ | MW. 185000 (93000) |
| BPO$_{40}$-poly-D-Glu$_{55}$-D-Lys$_{40}$-D-Tyr$_5$ | MW. 310000 (155000) |
| BPO$_{28}$-Suc$_{42}$-poly-D-Lys$_{70}$-D-Ala$_{30}$* | MW. 460000 (210000) |

*This style represents, for example, a polypeptide derivative whose peptide component is a copolymerisate of D-lysine and D-alanine in the ratio 70:30 and whose lysine side-chains carry benzylpenicilloyl and succinic acid groups in the ratio 40:60.

The novel polypeptide derivatives provided by the present invention can be manufactured in a manner known per se; namely by penicilloylating the polypeptide by reaction with a penicillin corresponding to the desired penicilloyl residue, preferably in the form of a well-soluble salt, in suitable proportions, in a suitable solvent.

The penicilloylation of the peptides can be carried out by simple incubation of the compounds, dissolved in alkaline medium, with the penicillin. In this case there results a stable linkage between the α-carboxyl group of the penicilloic acid and the amino groups of the carrier molecule [Schneider & de Weck, Helv. Chim. Acta 49, 1695 (1966)]. The penicilloylation procedure must be adapted having regard to the solubility situations. Under certain circumstances a previous partial succinylation of the carrier is advantageous on solubility grounds. The penicilloylation is preferably carried out in a moderately alkaline medium using an alkali salt of the penicillin employed, preferably the potassium salt. The penicilloylation of all amino groups (control with ninhydrin) must be carried out using an excess up to several times the theoretically required amount of penicillin.

The method given hereinafter can generally be used for the penicilloylation:

The peptide (100 mg.) is dissolved in 5 ml. of water, following which the pH is adjusted to 10.5 with 2-M K$_2$CO$_3$ solution. The appropriate amount of penicillin (advantageously in the form of the potassium salt) is introduced while stirring at room temperature in small portions, the pH being maintained constant by the addition of alkali. After termination of the reaction, the solution is neutralized with 1-N HCl and subjected to gel filtration in order to remove materials of low molecular weight. For most of the conjugates there can be used, for example, Sephadex-G-25 which is eluted with 0.01-M phosphate buffer (pH 7.4) or with water.

The conjugates are characterized by means of microgel determination and penamaldate analysis [Schneider & de Weck, Helv. Chim. Acta 49, 1689 (1966)]. Only fractions having stable penamaldate values are combined and lyophilized.

Examples 1 and 2 hereinafter describe in detail the manufacture of polypeptide derivatives provided by the present invention:

EXAMPLE 1

Manufacture of a conjugate from benzylpenicillin and a copolymerisate of D-glutamine, D-lysine and D-tyrosine (in the ratio 55:40:5, average MW. 155 000), each lysine group carrying a benzylpenicilloyl group (BPO$_{40}$-poly-D-Glu$_{55}$-D-Lys$_{40}$-D-Tyr$_5$)

100 Mg. of polypeptide are suspended in 5 ml. of water and the solution is stirred until a clear solution results. A total of 4 mmol of potassium benzylpenicillinate are introduced portionwise while stirring at pH 10.5. The spot test with ninhydrin is negative after 3 days, whereupon the solution is subjected to gel filtration through a Sephadex-G-25 column.

EXAMPLE 2

Manufacture of a conjugate from benzylpenicillin and poly-D-lysine (MW. 144 000) which is succinylated to 60% and penicilloylated to 30% (BPO$_{30}$-Suc$_{60}$-poly-D-Lys)

100 Mg. of poly-D-lysine hydrochloride are dissolved in 6 ml. of water and, after increasing the pH to 10.3 with 1-N NaOH, reacted with 0.4 mmol of succinic acid anhydride while maintaining the pH constant at 10.3. 1.87 mmol of potassium benzylpenicillinate are introduced portionwise into the slightly turbid solution, following which the mixture is stirred at room temperature for 100 hours at pH 10.5 and thereafter subjected to gel filtration through a Sephadex-G-25 column.

The polypeptide starting materials can be prepared from the amino acids according to methods which are generally known in peptide chemistry.

While the high molecular weight polypeptide starting materials are conveniently prepared by polycondensation, low molecular weight and medium molecular weight polypeptide starting materials can also be prepared by step-wise synthesis, that is to say, not only according to the classical methods but also according to the solid phase method.

Polycondensations with a single amino acid carboxyanhydride or with a mixture of various amino acid carboxyanhydrides are advantageously carried out in dimethylformamide or benzene/nitrobenzene (95:5). As the initiators there primarily come into consideration amino compounds containing primary or secondary amino groups and alcohlates such as, for example, sodium methoxide. The average chain length is approximately programmable by means of the chose molar ratio of carboxyanhydride to initiator. In the case of copolymers the ratio of the different carboxyanhydrides used mutually decides the amount of each amino acid in the polycondensate.

Poly-D-lysine$_{20}$ (average chain length 20 lysine units) can be prepared, for example, as follows:

70 G. (0.25 mol) of N$^\epsilon$-Z-D-lysine are suspended in 1.3 liters of dry ethyl acetate in a 2.5 liter four-necked flask equipped with a stirrer, thermometer, gas-inlet tube and reflux condenser. The mixture is heated to boiling and dry phosgene is conducted in until solution occurs (6–7 hours), the volume being maintained constant by the addition of solvent. After cooling to 35°–40° C., excess phosgene is driven off with dry nitrogen and the solution is concentrated to 400 ml. under reduced pressure. Addition of 900 ml. of dry n-hexane brings about the precipitation of N$^\epsilon$-Z-D-lysine carboxyanhydride which, after standing overnight, is filtered off under suction at 4° C. It is recrystallized from chloroform/hexane (12:5) and from ethyl acetate/n-hexane (4:3) and dried at −30° C. under reduced pressure.

5.1 G. (16.7 mmol) of N$^\epsilon$-Z-D-lysine carboxyanhydride are dissolved in 40 ml. of dimethylformamide (treated with K$_2$CO$_3$ with vacuum-distilled), treated with 0.155 g. (1.0 mmol) of the sodium salt of $\epsilon$-aminocaproic acid in 20 ml. of dimethylformamide and left to stand at room temperature for 65 hours. The solution is treated at 4° C. with 0.34 ml. of concentrated HCl in 100 ml. of water and stirred overnight. The separated product is centrifuged off, washed neutral with water and dried over P$_2$O$_5$. The product (3.6 g., yield 86%) is dissolved in 14.4 ml. of glacial acetic acid, mixed with 55 ml. of HBr in glacial acetic acid (33%) and stirred at room temperature overnight. Addition of 72 ml. of ether brings about separation of the decarbobenzyloxylated product which is filtered off under suction, washed with ether and dried under reduced pressure. There are obtained 2.85 g. of poly-D-lysine hydrobromide. The average chain length amounts to 20 lysine units. Its estimation is carried out by gel permeation chromatography in comparison with reference compounds or directly by ultracentrifugation.

Preparation of L-Lys$_4$-Gly-OEt according to the two-phase method—Schneider & Wirz, Helv. Chim. Acta 55, 1062 (1972)

Abbreviations: OEt: ethyl ester; OSu: hydroxysuccinimide ester; Et$_3$N: triethylamine; TFA: trifluoroacetic Acid; BOC: tert.butyloxycarbonyl; Z: benzyloxycarbonyl.

BOC-L-Lys (Z)-Gly-OEt 3.0 G. (6.28 mmol) of N$^\alpha$-BOC-N$^\epsilon$-Z-L-Lys-OSu are dissolved, together with 0.80 g. (5.7 mmol) of Gly-OEt.HCl, in 200 ml. of CH$_2$Cl$_2$ and treated with 975 $\mu$l of Et$_3$N. The solution is stirred at room temperature for 4 hours, treated with 3 mmol of picolylamine and further stirred for 1 hour. In accordance with the two-phase principle, the solution is washed with 0.1-N HCl or 0.5-M citric acid, then with water, with 0.3-M K$_2$CO$_3$ and once more with water. The solvent is then removed under reduced pressure and the residue dried. The yield amounts to 2.7 g. (100%).

TFA.L-Lys(Z)-Gly-OEt 2.7 G. (5.8 mmol) of the protected dipeptide prepared as described in the preceding paragraph are dissolved in 22 ml. of TFA and left to stand at room temperature for 45 minutes. The TFA is then removed under reduced pressure aNd the residue triturated with ether. The yield amounts to 2.44 g.

BOC-L-Lys(Z)-L-Lys(Z)-Gly-OEt 2.67 G. (5.6 mmol) of N$^\alpha$-BOC-N$^\epsilon$-Z-L-Lys-OSu and 2.44 g. of TFA.L-Lys(Z)-Gly-OEt are treated in 150 ml. of CH$_2$Cl$_2$ with Et$_3$N until the solution has a pH of 7. After stirring at room temperature overnight, 3 mmol of picolylamine are added and, after a further hour, the mixture is washed in accordance with the two-phase principle and worked-up. The residue weighs 3.32 g. (90%).

TFA.L-Lys(Z)-L-Lys(Z)-Gly-OEt 3.3 G. of the protected tripeptide prepared as described in the preceding paragraph are covered at 0° C. with 20 ml. of ice-cold TFA and stirred for 30 minutes. TFA is removed under reduced pressure and the residue triturated in ether. The yield amounts to 3.6 g.

BOC-L-Lys(Z)-L-Lys(Z)-L-Lys(Z)-Gly-OEt 2.2 G. (4.6 mmol) of N$^\alpha$-BOC-N$^\epsilon$-Z-L-Lys-OSu and 3.38 g. of N$^\alpha$-deblocked tripeptide from the previous step are treated in 150 ml. of CH$_2$Cl$_2$ with 4.6 mmol of Et$_3$N and stirred at room temperature overnight. 2.5 mmol of picolylamine are added to the milky turbid solution. 1 Hour later the mixture is extracted in accordance with the two-phase principle and worked-up. The yield amounts to 3.26 g. (72%).

TFA.L-Lys(Z)-L-Lys(Z)-L-Lys(Z)-Gly-OEt 3.25 G. of the protected tetrapeptide obtained according to the preceding paragraph are dissolved at 0° C. in 20 ml. of TFA and left to stand for 30 minutes. After removal of the TFA under reduced pressure, the residue is tritruated with ether. The yield amounts to 3.5 g.

BOC-L-Lys(Z)-L-Lys(Z)-L-Lys(Z)-L-Lys(Z)-Gly-OEt 1.6 g. (3.3 mmol) of N$^\alpha$-BOC-N$^\epsilon$-Z-L-Lys-OSu and 3.5 g. of N$^\alpha$-deblocked tetrapeptide from the previous step are dissolved in 150 ml. of CH$_2$Cl$_2$ and 40 ml. of dimethylformamide and treated with Et$_3$N until the solution has a pH of 7. 4 Hours later 2 mmol of picolylamine are introduced while stirring and, after a further hour, the solution is extracted in accordance with the two-phase principle and worked-up. The residue is finally precipitated from methyl ethyl ketone/ether. The yield amounts of 3.0 g. (73%).

HBr.L-Lys(HBr)-L-Lys(HBr)-L-Lys(HBr)-L-Lys(HBr)-Gly-OEt 3 g. of the protected pentapeptide obtained as described in the preceding paragraph are treated at 0° C. with 30 ml. of glacial acetic acid and, while stirring well, with 145 ml. of HBr in glacial acetic acid (33%). The solution is stirred for 45 minutes and then precipitated with 900 ml. of ether. The precipitate is filtered off under suction, washed with ether and dried over KOH under reduced pressure. The yield amounts to 2.15 g.

The material neutralized with NaOH is subjected to a multiple Craig's distribution over 206 layers in the system n-butanol/ethanol/0.05% acetic acid (4:1:5 v/v). The main fraction shows the following amino acid composition: Gly: 0.94; Lys$_4$: 4.06.

The polypeptide derivatives provided by the present invention are useful as medicaments by means of which a human or animal organism can be made tolerant specifically towards penicilloyl antigens. Thereby, the organism initially rapidly loses its capability to react towards penicilloyl antigens by means of specific antibodies and moreover tolerates renewed introduction of penicilloyl antigens without producing significant amounts of anti-penicilloyl antibodies and without showing allergic manifestations which might be introduced by such antibodies. Pertinent results can be obtained with experiments on mice and guinea pigs.

If a sufficiently small dosage of BPO-tolerogen is given to mice (e.g. of the C$_3$H-strain), which have been immunized with benzylpenicilloylated bovine gamma-globulin (BPO-BGG) in complete Freund's adjuvant and have produced antibodies not only against the BPO group but also against determinants of the globulin, then the anti-BPO-antibodies disappear from the serum of the mice after a few days. Several booster injections of BPO-BGG administered during the course of several weeks lead to no renewed appearance of anti-BPO-antibodies. In contrast to this, anti-BGG-antibodies remain measurable after the tolerogen administration; their titre increases afer each of the booster injections of BPO-BGG. Virtually identical results are obtained when the BPO-tolerogen is injected into animals which are immunized for the first time shortly thereafter. The tolerance induction accordingly succeeds not only in specifically sensitized organisms but also in non-sensitized organisms.

When being used in sensitized organisms the present compounds may advantageously be administered together with an antiallergic. Examples of such antiallergic agents are prednisolone and other steroids which generally are administered i.v., antihistaminics such as thenaldine and dimetindene or N$^6$-(benzyl-α-penicilloyl)-N$^2$-formyl-L-lysine.

For example, the action of the BPO-tolerogen BPO$_{20}$-D-Lys$_{20}$ is reproduced in detail in FIG. 1 hereinafter. The given anti-BPO-antibody titres were measured by means of the BPO-phage neutralization test [Lazary et al. Path. Microbiol. 38, 6 (1972)]. Similar curves are obtained when the BPO-Ala-H$^3$-formation test [Otz et al., Chimia 30, 89 (1976)] is used. While the anti-BPO titres in animals which receive no tolerogen or only carrier without haptan (succinylated Lys$_{20}$) are stimulated by the booster injections as compared with increased antibody production of the primary stimulation and the BPO-phage titres show about 1/10000, the animals which receive 3.65 mg. of tolerogen no longer show significant amounts of antibodies. The titre in the very sensitive phage test falls to an insignificant value between 1/10 and 1/100. The less sensitive BPO-Ala-H$^3$-formation test yields completely negative values. The animals which receive 0.36 mg. of tolerogen show a titre increase after the 2nd boost and there appear a strong anti-BPO-antibody production after the 4th boost which is carried out 26 weeks following the primary stimulation. This is eliminated by administration of additional tolerogen (a further 0.36 mg). The 6th boost does not bring about renewed stimulation of the antibody formation. Only the 7th boost effected 50 weeks after primary immunization appears to bring about anti-BPO-antibody formation in all tolerogen-treated animals and accordingly appears to indicate a termination of the tolerance.

In order to compare the activity of the various tolerogens it is necessary to provide a definition of the activity factor, this being in essence based on the quotient antibody titre of immunized animal/antibody titre of tolerogen-treated animal at a suitable point in time.

Activity of BPO-$_{20}$-D-Lys$_{20}$ on anti-BPO-antibody production in C$_3$H mice as demonstrated by FIG. 1.

The mice were immunized with BPO-BGG in complete Freund's adjuvant (in each 25 g of immunogen injected subcutaneously in the hind paws). Booster injections ( ↑ ) (100 μg of immunogen in 0.3 ml. of 0.9% NaCl) carried out intraperitoneally. This protocol was carried out on 4 groups each comprising 8 mice. Serum from 4 animals was obtained and combined for the titre determination in the case of each measurement value. Group I(0): immunogen administration only; Group II(0): after 8 weeks there were injected intrperitoneally 33 nanomol of completely succinylated D-lys$_{20}$ in phosphate-buffered 0.9% NaCl solution, pH 7.4 (PBS); Group III(0): after 8 weeks there were injected intraperitoneally 3.65 mg. of BPO$_{20}$-D-Lys$_{20}$ in PBS(To); Group IV(0): after 8 and 29 weeks there was injected intraperitoneally 0.36 mg. of BPO$_{20}$-D-Lys$_{20}$ in PBS(To or To*).

The activity factor W used herein in connection with the BPO tolerogens is defined as follows:

$$W = \frac{1}{2} \sum_{I-II} \frac{\text{anti-BPO-titre of immunized animal}}{\text{anti-BPO-titre of tolerized animal}} \quad (1)$$

wherein I represents the titre from the sample bleedings one week after the first booster injection and II represents the corresponding titre after the 2nd booster injection, which in each case is effected one week after the first booster injection.

Values of around one indicate no activity, whereas high values indicate good activity. It will, of course, be appreciated that technically a limit is placed by the sensitivity of the titre determination.

Table

| Activity factor (W) of BPO tolerogens in immunized mice | | | |
|---|---|---|---|
| Tolerogen | MW | mg | W |
| BPO$_{20}$-D-Lys$_{20}$ | 3000 | 3.65 | 425 |
|  |  | 0.36 | 65 |
| BPO$_{20}$-L-Lys$_{20}$ | 3000 | 0.3 | 30 |
| BPO$_{20}$-Suc$_{60}$-poly-D-Lys | 150000 | 2.5 | 137 |
| BPO$_{38}$-poly-D-Glu$_{48}$-D-Lys$_{38}$-D-Tyr$_{14}$ | 160000 | 0.78 | 333 |
| BPO$_{39}$-poly-D-Glu$_{55}$-D-Lys$_{39}$-D-Tyr | 93000 | 0.45 | 126 |

The polypeptide derivatives provided by the present invention can accordingly be used as medicaments in the form of pharmaceutical preparations which contain them in association with a compatible pharmaceutical carrier material. This carrier material can be an organic or inorganic non-toxic inert carrier material suitable for enteral or parenteral administration such as, for example, water, gelatin, gum arabic, lactose, starch, magnesium stearate, talc, vegetable oils, polyalkyleneglycols, petroleum jelly and the like. The present pharmaceutical preparations are preferably administered parenterally. The pharmaceutical preparations can be made up in solid form (e.g. as tablets, dragees or capsules) or in liquid form (e.g. as solutions, suspensions or emulsions). The pharmaceutical preparations may be sterilized and/or may contain adjuvants such as preserving, stabilizing, wetting or emulsifying agents, flavor-improving agents, salts for varying the osmotic pressure or substances acting as buffers. The pharmaceutical preparations can be prepared in a manner known per se by mixing a polypeptide derivative provided by the present invention with a compatible pharmaceutical carrier material of the type mentioned earlier and transforming the resulting mixture into the desired unitdosage form.

The dosages in which the polypeptide derivatives provided by the present invention are administered will depend upon individual requirements. As a guideline, the polypeptide derivatives can be administered once or repeatedly in an amount of 1 µg-10 mg/kg body weight.

We claim:

1. The polypeptide derivative: $BPO_{20}$-D-$Lys_{20}$ having an average molecular weight of 9240 to which are bound via its functional side chains penicilloyl residues of the formula

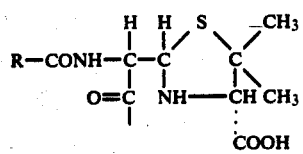

wherein R signifies 2-pentenyl, n-pentyl, n-heptyl, allylthiomethyl, 5-amino-5-carboxypentyl, benzyl, α-carboxybenzyl, α-aminobenzyl, phenoxybenzyl, phenoxymethyl, α-phenoxyethyl, α-phenoxypropyl, 2,6-dimethoxyphenol, 2-ethoxy-1-naphthyl, 3-carboxy-2-quinoxazinyl, 5-methyl-3-phenyl-4-isoxazolyl, α-amino-p-hydroxybenzyl, 3-(2-chlorophenyl)-5-methyl-4-isoxazolyl, 3-(2,6-dichlorophenyl)-5-methyl-4-isoxazolyl, 3-(2-chloro-6-fluorophenyl)-5-methyl-4-isoxazolyl, α-carboxy-3-thienylmethyl or α-sulphonylbenzyl.

2. The polypeptide derivative: $BPO_{20}$-L-$Lys_{20}$ having an average molecular weight of 9240.

3. The polypeptide derivative: $BPO_5$-$Suc_{15}$-D-$Lys_{20}$ having an average molecular weight of 5730.

4. The polypeptide derivative: $BPO_5$-L-$Lys_4$-Gly having an average molecular weight of 2259.

5. The polypeptide derivative: $BPO_{40}$-$Suc_{60}$-poly-D-Lys having an average molecular weight of 380,000.

6. The polypeptide derivative: $BPO_{38}$-poly-D-$Glu_{48}$-D-$Lys_{38}$-D-$Tyr_{14}$ having an average molecular weight of 310,000.

7. The polypeptide derivative: $BPO_{39}$-poly-D-$Glu_{55}$-D-Lys-39-D-$Tyr_6$ having an average molecular weight of 185,000.

8. The polypeptide derivative: $BPO_{40}$-poly-D-$Glu_{55}$-D-$Lys_{40}$-D-$Tyr_5$ having an average molecular weight of 310,000.

9. The polypeptide derivative: $BPO_{28}$-$Suc_{42}$-poly-D-$Lys_{70}$-D-$Ala_{30}$ having an average molecular weight of 460,000.

* * * * *